United States Patent [19]
Weissman et al.

[11] Patent Number: 6,092,530
[45] Date of Patent: Jul. 25, 2000

[54] REMOTELY INTERROGATED IMPLANT DEVICE WITH SENSOR FOR DETECTING ACCRETION OF BIOLOGICAL MATTER

[75] Inventors: Eric M. Weissman, Chagrin Falls, Ohio; William B. Spillman, Jr., Charlotte, Vt.; Elmer D. Dickens, Jr., Richfield, Ohio

[73] Assignee: The B.F. Goodrich Company, Akron, Ohio

[21] Appl. No.: 09/275,166

[22] Filed: Mar. 24, 1999

[51] Int. Cl.[7] .................................................. A61B 19/00
[52] U.S. Cl. ............................................ 128/899; 128/903
[58] Field of Search ...................... 607/60–63; 600/309, 600/345, 347–348, 364–366, 372–381; 128/899, 903

[56] References Cited

U.S. PATENT DOCUMENTS

| | | |
|---|---|---|
| 4,227,407 | 10/1980 | Drost . |
| 4,453,537 | 6/1984 | Spitzer . |
| 5,305,758 | 4/1994 | Dietz et al. . |
| 5,306,644 | 4/1994 | Myerholtz et al. . |
| 5,358,514 | 10/1994 | Schulman et al. . |
| 5,372,133 | 12/1994 | Hogen Esch . |
| 5,411,551 | 5/1995 | Winston et al. . |
| 5,620,475 | 4/1997 | Magnusson . |
| 5,663,507 | 9/1997 | Westervelt et al. . |
| 5,709,225 | 1/1998 | Budgifvars et al. . |
| 5,720,771 | 2/1998 | Snell . |
| 5,735,887 | 4/1998 | Barreras, Sr. et al. . |
| 5,741,315 | 4/1998 | Lee et al. . |
| 5,807,258 | 9/1998 | Cimochowski et al. . |
| 5,833,603 | 11/1998 | Kovacs et al. . |

FOREIGN PATENT DOCUMENTS 9829030  7/1998  WIPO .

OTHER PUBLICATIONS

"Sensing and Processing for Smart Structures", W. B. Spillman, Jr.; Proceedings of the IEEE, vol. 84, No. 1, Jan. 1996 pp 68–77.

"Bio –Medical Telemetry Sensing and Transmitting Biological Information From Animals and Man"; R. Stuart Mackay; IEEE Press; (e.g., pp 69–70 and pp 298–315).

Primary Examiner—Cary O'Connor
Assistant Examiner—Ryan Carter
Attorney, Agent, or Firm—Brian M. Kolkowski; Mark D. Saralino

[57] ABSTRACT

An implant device which includes a structure implantable within a living animal and a sensor included as part of the structure. The sensor is operatively configured to detect accretion of biological material on the sensor by producing an output which varies as a function of the accretion of biological material on the sensor. A communication element is further included as part of the structure and is operatively coupled to the output of the sensor. The communication element is configured to communicate information based on the output of the sensor wirelessly to a remote element located outside the living animal.

17 Claims, 4 Drawing Sheets

REMOTELY INTERROGATED IMPLANT DEVICE WITH SENSOR FOR DETECTING ACCRETION OF BIOLOGICAL MATTER

TECHNICAL FIELD

The present invention relates generally to medical implant devices, and more particularly to devices which may be interrogated remotely from outside the body.

BACKGROUND OF THE INVENTION

Various types of medical implant devices have been developed over the years. In many instances, such devices enable humans to live longer, more comfortable lives. Implant devices such as pacemakers, artificial joints, valves, grafts, stents, etc. provide a patient with the opportunity to lead a normal life even in the face of major heart, reconstructive, or other type surgery, for example.

It has been found, however, that the introduction of such implant devices can sometimes lead to complications. For example, the human body may reject the implant device which can ultimately lead to infection or other types of complications. Alternatively, the implant device may malfunction or become inoperative. Therefore, it is desirable to be able to monitor the condition of the implant device. On the other hand, it is highly undesirable to have to perform invasive surgery in order to evaluate the condition of the device.

Still further, it is desirable to be able to monitor conditions related to the use of implant devices. For example, in heart patients it may be helpful to know the extent of occlusion in a stent or graft in order to evaluate the health of the patient. Again, however, it is undesirable to have to perform invasive surgery in order to evaluate such conditions.

Techniques have been developed which enable the function of an implant device to be monitored remotely from outside the body of the patient. These techniques involve including one or more sensors in the device for sensing the condition of the device. The device further includes a small transceiver for processing the output of the sensors and transmitting a signal based on the output. Such signal typically is a radio frequency signal which is received by a receiver from outside the body of the patient. The receiver then processes the signal in order to monitor the function of the device.

Micro-miniature sensors have been proposed for use in implant devices. For example, PCT Application WO 98/29030 to Govari et al. discusses the use of piezoelectric pressure sensors or micro-machined silicon strain gages in a stent. Pressure changes from one sensor to another are considered indicative of constriction of the stent. U.S. Pat. No. 5,807,258 to Cimochowski et al. describes using surface acoustic wave (SAW) sensors in a graft. Transit times or Doppler measurements using the SAW sensors enable one to determine fluid flow or velocity.

In each such case, however, the amount of constriction (i.e., build up of restenosis or other biological matter) can only be inferred and is not directly measured. For example, blood flow or velocity may not be noticeably affected until after the build-up of a significant amount of restenosis. This can lead to false diagnoses and/or require occlusion be in a more advanced state prior to detection. Furthermore, measurements based on transit times or Doppler measurements, for example, can require complex processing which expose such approaches to another source for error.

In view of the aforementioned shortcomings associated with conventional implant devices, there is a strong need in the art for a medical implant device which can detect the buildup of biological matter more directly compared to conventional devices. There is a strong need for a medical implant device which can provide an indication of the amount of occlusion, extent of infection, etc. more directly and which can be remotely interrogated simply and reliably.

SUMMARY OF THE INVENTION

The present invention is responsive to the aforementioned shortcomings with conventional devices, and is directed towards an implant device to be implanted within a living animal. One or more sensors are included in the device and serve to detect directly the amount of biological material such as restenosis which builds up on the sensors. This provides a direct indication of the amount of biological material which may be occluding a vein or artery, for example. The output of the sensor is coupled to a communication element which communicates information to a remote element outside the living animal so that the information may be processed to provide a diagnosis.

In such manner, the present invention does not require the calculation of transit times, Doppler measurements or pressure gradients between different sensors in order to be able to infer the amount of build up of biological material. Rather, the build up of biological matter on a given sensor itself is detected to indicate more directly the occurrence of restenosis, etc.

In one embodiment, the implant device includes a SAW sensor. The output of the sensor is designed to be a function of the amount of biological material which builds up on the surface of the sensor. More specifically, the output of the sensor varies as the accretion of biological material increases. For example, the accretion of biological material alters the extent to which the surface acoustic wave is able to couple energy to the surrounding medium within the body of the living animal.

In another embodiment, the implant device includes a microelectrical-mechanical sensor (MEMs) device, hereinafter referred to as a MEMs sensor. The MEMs sensor in a preferred embodiment includes at least one cantilever beam. The amount of build up of biological matter on the cantilever beam varies the output of the sensor, so as to provide an indication of the amount of accretion.

According to one particular aspect of the invention, an implant device is provided which includes a structure implantable within a living animal; a sensor included as part of the structure, the sensor being operatively configured to detect accretion of biological material on the sensor by producing an output which varies as a function of the accretion of biological material on the sensor; and a communication element included as part of the structure and operatively coupled to the output of the sensor, the communication element being configured to communicate information based on the output of the sensor wirelessly to a remote element located outside the living animal.

In accordance with another aspect of the invention, a diagnostic system is provided which includes a structure implantable within a living animal; a sensor included as part of the structure, the sensor being operatively configured to detect accretion of biological material on the sensor by producing an output which varies as a function of the accretion of biological material on the sensor; a communication element included as part of the structure and operatively coupled to the output of the sensor, the communication element being configured to communicate information based on the output of the sensor wirelessly to a remote element located outside the living animal; the remote element configured to receive the information from the communication element outside the living animal; and a processor for processing the information received by the remote element based on the function to provide a diagnostic output.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DESCRIPTION OF THE PREFERRED EMBODIMENT

Figure 1:
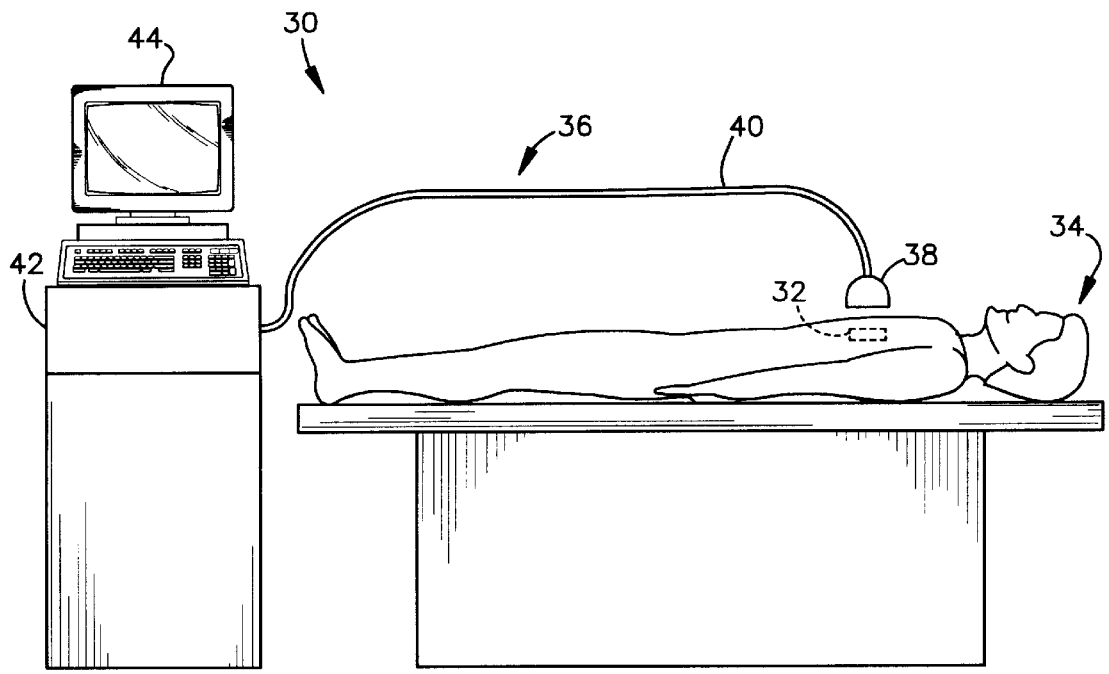
FIG. 1 is an environmental view illustrating a system including a remotely interrogated medical implant device and exciter/interrogator unit in accordance with the present invention.

The present invention will now be described with reference to the drawings, wherein like reference numerals are used to refer to like elements throughout.

Referring initially to FIG. 1, a system for remotely interrogating a medical implant device in accordance with the invention is generally designated 30. The system 30 includes a medical implant device 32 which is implanted in a living animal such as a human patient 34. The medical implant device 32 can be any of a wide variety of different types of devices including, for example, a stent, graft, artificial joint, etc.

The device 32 is configured typically to carry out or assist in carrying out a function within the patient 34. For example, in the case of a stent the device 32 prevents the closing of a wall of a blood vessel and permits the flow of blood therethrough. In the case of a graft, the device 32 serves to couple blood flow between two separate ends of a blood vessel. The device 32 may instead, for example, consist of an artificial hip or knee which facilitates movement of the leg of the patient 34. Other functions include, but are not limited to, a hemodialysis shunt and spinal brace, for example.

The device 32 includes a sensing circuit (not shown in FIG. 1) having a sensor which serves to sense accretion of biological material. Such biological material may be associated with the function performed by the device. For example, in the case of a stent or graft the sensor may be used to detect the degree of restenosis which occurs within the device 32. As is known, biological matter such as restenosis can build up on the walls of the stent or graft and can lead to partial and/or total occlusion of the vessel. The sensor detects such build up and, in combination with the sensing circuit, wirelessly communicates such information to a remote location outside the body of the patient.

The system 30 further includes interrogation instrumentation 36 for remotely interrogating or otherwise receiving information from the implant device 32 in order to evaluate the device function. The instrumentation 36 includes an exciter/interrogator unit 38 which is positioned outside the patient 34 in close proximity to the implant device 32. The exciter/interrogator unit 38 is coupled via an electrical cable 40 to the main circuitry 42 included in the interrogation instrumentation 36. The main circuitry 42 includes suitable circuits for driving the exciter/interrogator unit 38 as described below, and for processing the output of the exciter/interrogator unit 38 in order to provide an output to an operator (e.g., display 44).

The exciter/interrogator unit 38 preferably is a hand-held sized device which is held by a doctor, nurse or medical assistant in close proximity to the implant device 32. Since the system 30 is non-invasive, the exciter/interrogator unit 38 may be placed adjacent the implant device 32 with the body of the patient (e.g., skin, muscle tissue, etc.) disposed therebetween. The preferred embodiment of the present invention relies on magnetic and/or electromagnetic coupling between the exciter/interrogator unit 38 and the implant device 32 to interrogate the device 32 non-invasively.

Alternatively, other forms of non-invasive means for communicating information from the implant device 32 to the instrumentation 36 are available without departing from the scope of the invention. For example, the implant device 32 may include a high-frequency radio transmitter which serves to transmit a signal which is received and processed by the instrumentation 36. Alternatively, sonic coupling between a sonic transducer included in the implant device 32 and one in the exciter/interrogator unit 38 may also serve as a viable approach to communications between the implant device 32 and the instrumentation 36.

The present invention is not intended to be limited to a particular non-invasive communication format, whether it be magnetic or electromagnetic coupling, radio frequency communications, sonic coupling, etc. Sufficient information which would allow a person having ordinary skill in the art to make and use a particular communication format can be found, for example, in U.S. Pat. No. 5,807,258, PCT Application WO 98/29030, and in commonly assigned and concurrently filed U.S. patent application Ser. Nos. 09/275,308 and 09/275,311 entitled "Remotely Interrogated Diagnostic Implant Device with Electrically Passive Sensor", and "Acoustic-Based Remotely Interrogated Diagnostic Implant Device and System", respectively, each to Spillman et al.

The entire disclosures of the patent and patent applications are hereby incorporated herein by reference. Accordingly, additional detail has been omitted for sake of brevity.

Figure 2:
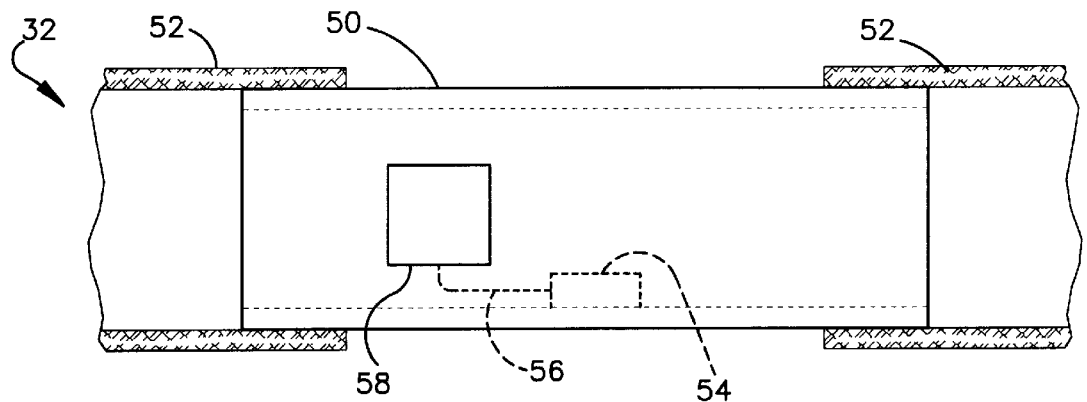
FIG. 2 is a side view of a remotely interrogated graft in accordance with one embodiment of the present invention.

FIG. 2 represents an implant device 32 which is a graft according to an exemplary embodiment of the present invention. The graft 32 has a tube shaped structure 50 and is surgically inserted and secured between two ends of a blood vessel 52 as is conventional. As is known, the graft 32 serves to permit blood flow between the respective ends of the vessel 52. The structure of the graft 50 may be made of metal, plastic, a composite material, etc.

The graft 50 includes a sensor 54 which is mounted on or in an inner wall of the tube as shown in FIG. 2. Although not shown, the sensing surface of the sensor 54 preferably is flush with the wall to minimize obstruction of flow. As is discussed below in relation to FIGS. 4–6 and 8–10, for example, the sensor 54 serves to produce an output which varies as a function of the accretion of biological material on a surface thereof. The sensor 54 is connected by way of wires 56 to a main circuit 58 formed within a sealed housing and mounted to an outer wall of the tubular structure 50, for example.

Figure 3:
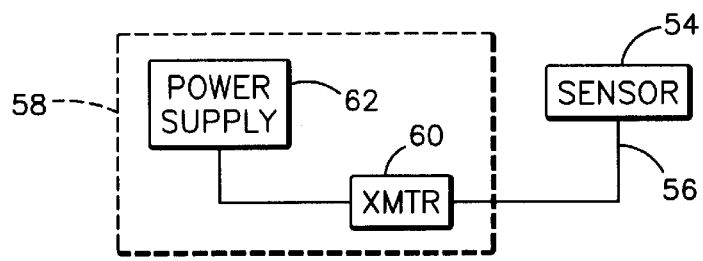
FIG. 3 is a block diagram of the electronic circuitry included within the graft of FIG. 2.

As shown in FIG. 3, the main circuit 58 in the exemplary embodiment includes a miniature transmitter 60 and a power supply 62. The transmitter 60 is designed to transmit a signal which is encoded with information based on the output of the sensor 54. The transmitter 60 may utilize virtually any magnetic, electromagnetic, radio frequency, sonic, or other means of communications for transmitting the information received from the sensor 54 to the exciter/interrogator unit 38 outside the patient 34 without departing from the scope of the invention. For example, the techniques described in the aforementioned U.S. Pat. No. 5,807,258, PCT Application WO 98/29030, and U.S. Patent Applications entitled "Remotely Interrogated Diagnostic Implant Device with Electrically Passive Sensor", and "Acoustic-Based Remotely Interrogated Diagnostic Implant Device and System" may be employed.

In the exemplary embodiments, the transmitter 60 provides an alternating current (AC) excitation signal to the sensor 54 via wires 56. The transmitter 60 receives as the output from the sensor 54 its response to the excitation signal (e.g., by variation in load, energy loss, change in resonant frequency, etc. across wires 56). The transmitter 60 then transmits a signal containing information based on the response of the sensor 54 to the exciter/interrogator unit 38 and/or the main circuitry 42.

The power supply 62 provides operating power to the transmitter 60 and/or the sensor 54, as needed. The power supply 62 may be a battery, a charge storing capacitor, etc. Power may be provided externally to the power supply 62 via magnetic or electromagnetic energy, for example, as discussed in the aforementioned patent and patent applications. Alternatively, the main circuit 58 and sensor 54 may make up an electrically passive device as described in the above-mentioned U.S. Patent Application entitled "Remotely Interrogated Diagnostic Implant Device with Electrically Passive Sensor", for example.

Figure 4:
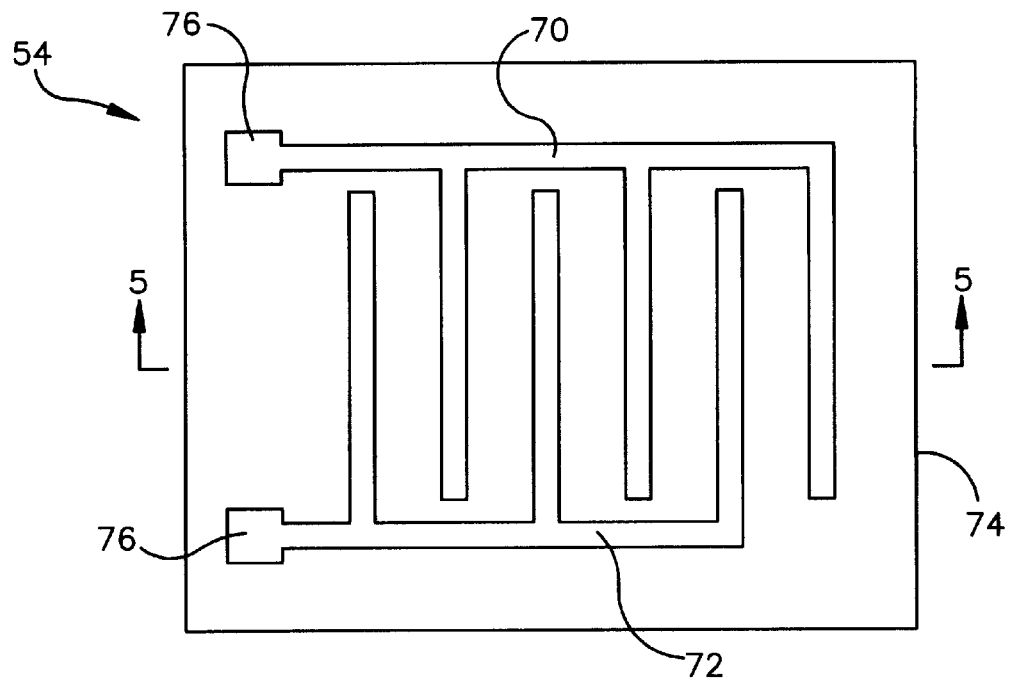
FIG. 4 is a top view of a SAW sensor used in accordance with the present invention.
Figure 5:
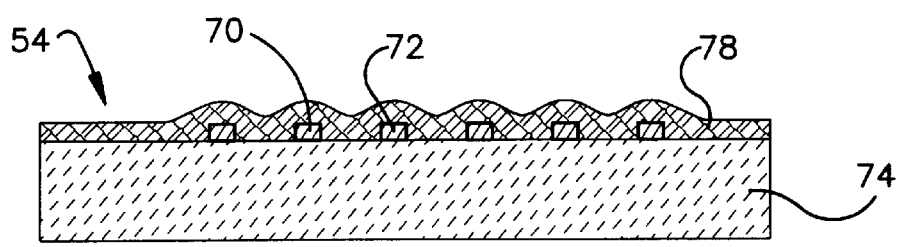
FIG. 5 is a cross-section view of the SAW sensor of FIG. 4 taken along line 5—5.

Referring now to FIGS. 4 and 5, a first embodiment of the sensor 54 is illustrated. In this embodiment, the sensor 54 is a SAW type device. The sensor 54 includes a pair of interdigitated electrodes 70 and 72 formed on a piezoelectric material substrate 74. The electrodes 70 and 72 are formed of a conductive material such as copper, polysilicon, indium tin oxide, etc., typically found in the fabrication of integrated circuits.

The electrodes 70 and 72 are formed on the substrate 74 using any suitable fabrication technique such as photolithography, ion-etching, etc. Each electrode 70 and 72 includes a pad 76 for providing an electrical connection to the transmitter 60 via the wires 56. Using known techniques for producing a SAW sensor, the sensor 54 can be made very small—on the order of one hundred microns thick and two millimeters squared in area.

In one particular embodiment, the transmitter 60 provides an RF electrical excitation signal to the sensor 54 which in turn generates an ultrasonic acoustic wave at the surface of the sensor 54. Depending on the amount of biological material (e.g., restenosis) which has built up on the surface of the sensor 54, the amount of energy which is coupled to the blood flowing through the graft 50 in response to the excitation signal varies. As relatively solid biological material adheres to the sensor 54, the output of the sensor 54 will change as less energy is coupled into the liquid blood.

Figure 6:
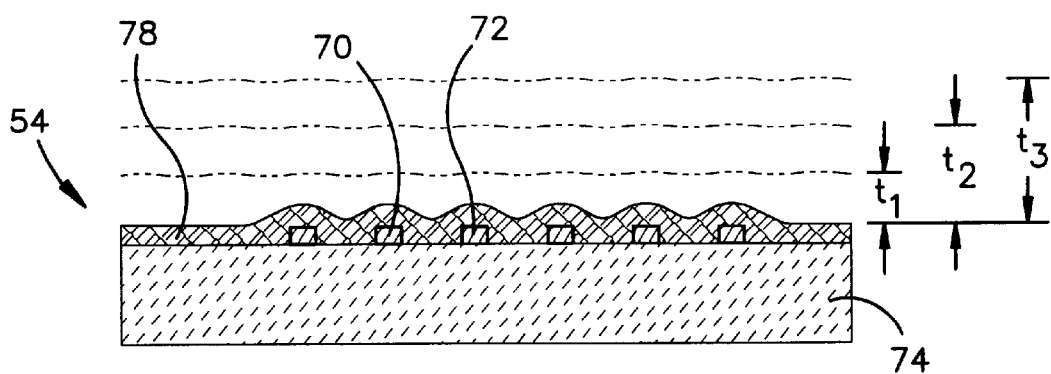
FIG. 6 is a cross-section view of the SAW sensor as in FIG. 5, with dashed lines illustrating different degrees of accretion in accordance with the present invention.
Figure 7:
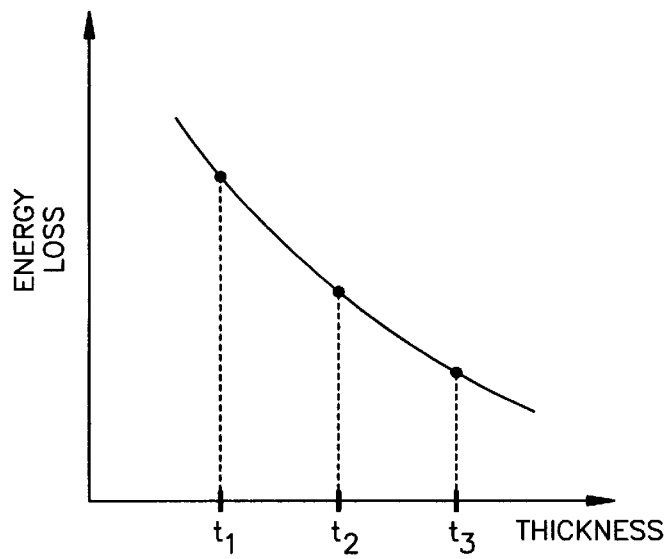
FIG. 7 is a graph illustrating an exemplary simplified function relating the output of the SAW sensor with the degree of accretion in accordance with the present invention.
Figure 7A:
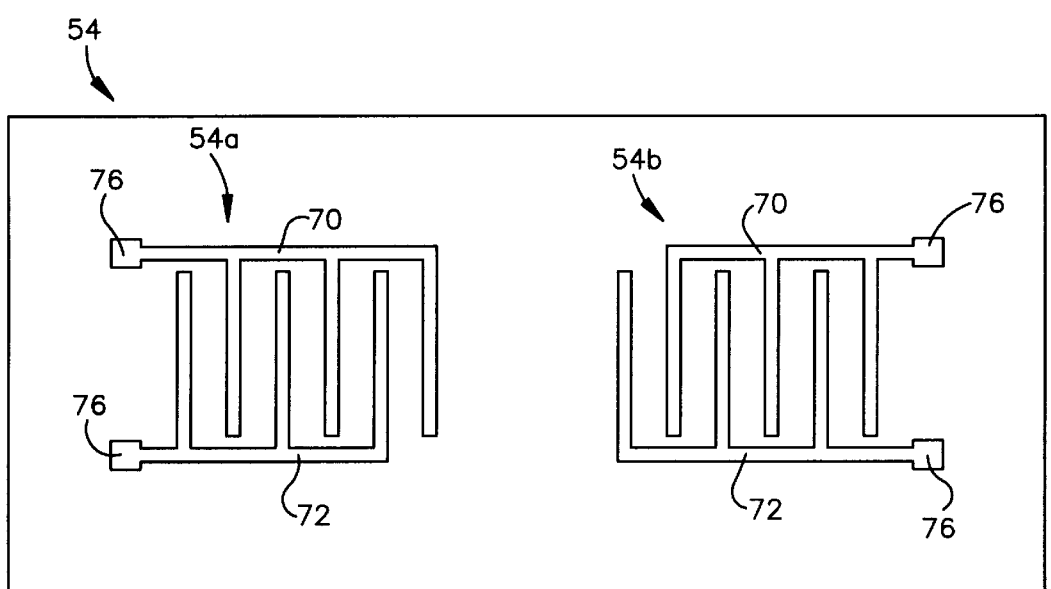
FIG. 7A is a top view of a SAW sensor in accordance with another embodiment of the present invention.

FIG. 6 illustrates how different thicknesses (e.g., t1, t2, and t3) of biological matter may build up on the surface of the sensor 54. FIG. 7 shows in a simplified manner how the energy loss of the sensor 54 decreases as the buildup of biological material increases in thickness. Such information thus becomes indicative of the thickness of the biological material, and hence the amount of buildup. The main circuitry 42 is programmed to analyze the output of the sensor 54 by correlating the output of the sensor 54 to a function such as that shown in FIG. 7 to determine the degree of biological buildup.

In another embodiment, the structure of the SAW sensor 54 can be designed such that the energy of the excitation signal couples better to the relatively solid biological matter compared to the liquid blood. Thus, as the amount of buildup increases the energy loss incurred by the sensor 54 similarly increases.

The amount of buildup of biological material can also be related to the wave speed, frequency or phase of the SAW sensor 54 output. Accordingly, by analyzing the wave speed, frequency or phase of the SAW sensor 54 output based on a predefined criteria similar results may be obtained.

According to still another version of the SAW sensor 54, a pair of individual SAW elements 54a and 54b each having a construction similar to that shown in FIG. 4 are provided on the substrate 74. The individual SAW elements 54a and 54b are configured adjacent each other such that the transit time of the ultrasonic wave from one electrode to another is used to evaluate the amount of buildup of biological matter. An excitation signal from the transmitter 60 is applied to the electrodes 70 and 72 of the SAW element 54a which generates an ultrasonic wave which travels on the surface of the sensor 54 to the SAW element 54b. The SAW element 54b in turn converts the ultrasonic wave back into an electrical signal across electrodes 70 and 72 which is provided to the transmitter 60. The transit time of the wave between the elements 54a and 54b is a function of the mass and modulus of material at the surface of the sensor 54. Thus, as biological material accretes on the surface the transit time will change. The transmitter 60, in such an embodiment, measures the transit time and transmits the information to the main circuit 42. It is noted that in such embodiment, the transit time is not used to compute blood flow velocity, but rather the local buildup of biological matter.

In the exemplary embodiment, the surface of the sensor 54 is coated with a very thin layer 78 of the same or similar material from which the body of the graft 50 is also made or coated. In this way, the sensor 54 itself will tend not to create an atypical environment which may promote restenosis or other build up at a rate different from that occurring in the remainder of the graft 50. Exemplary types of coatings include nylon, collagen and PTFE which are commonly used to make grafts.

Alternatively, a coating may be used which allows the tailoring of the rate at which the build up of biological matter occurs at the sensor 54 relative to elsewhere in the graft 50. This allows one to scale the dynamic range of the sensor 54 relative to the range of the accretion process. Examples of such coatings include hemocompatible coatings such as carbon or diamond-like carbon or polymers modified with chemicals to improve hemocompatibility (e.g., heparin containing polymer coatings); hemosorbent coatings; or bound inhibitor coatings.

Figure 8:
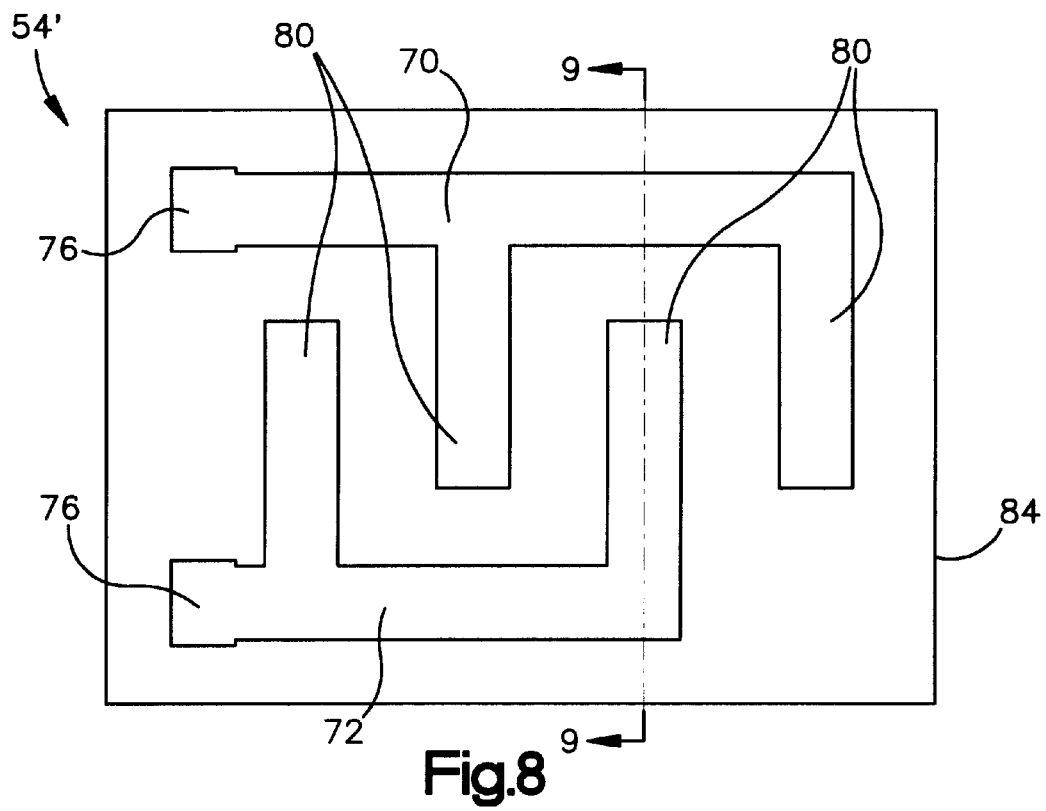
FIG. 8 is a top view of a MEMs sensor used in accordance with the present invention.
Figure 9:
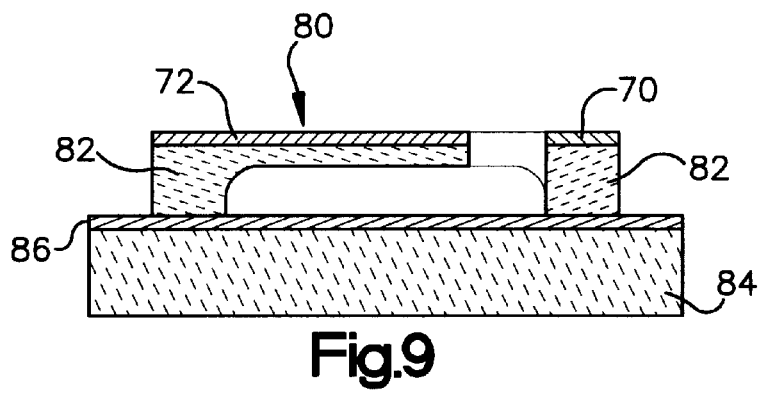
FIG. 9 is a cross-section view of the MEMs sensor of FIG. 8 taken along line 9—9.

FIGS. 8 and 9 illustrates another embodiment of the sensor 54 (designated by 54') in which the sensor 54' is a MEMs device. The sensor 54' includes a plurality of cantilevered beams 80 formed on the surface of the sensor. Each cantilevered beam 80 is formed, in part, by a corresponding leg of the interdigitated electrodes 70 and 72. The electrodes 70 and 72 are formed on a piezoelectric material substrate 82. Using known techniques for fabricating MEMs devices, the substrate 82 is etched or otherwise removed beneath the legs of the electrodes as shown in FIG. 9 to produce the cantilevered beam 80.

Figure 10:
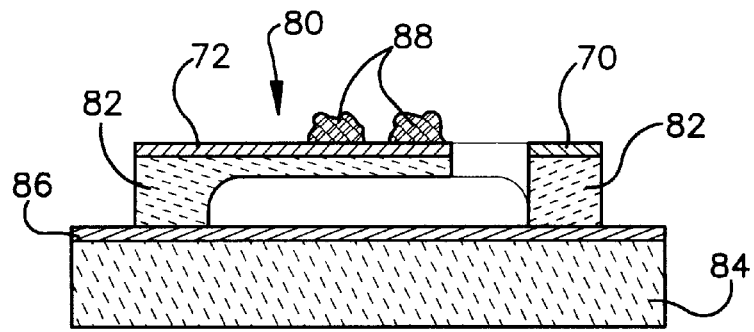
FIG. 10 is a cross-section view of the MEMs sensor as in FIG. 9, and additionally illustrating the build up of biological material thereon.

The cantilevered beams 80 are formed on a substrate 84 with a common electrode 86 disposed between the substrates 82 and 84. The dynamic strain response of a given cantilevered beam 80 with regard to an excitation signal applied across the respective electrode 70,72 and the common electrode 86 will be a function of the accreted mass on the surface of the sensor 54 due to restenosis or the biological matter or interest. For example, FIG. 10 illustrates the buildup of biological matter 88 on a cantilevered beam 80.

The transmitter 60 provides the excitation signal to the sensor 54' via the wires 56, and detects the dynamic response via phase and/or amplitude of the signal received back from the sensor 54'. The transmitter 60 then transmits such information to the main circuit 42 which in turn is programmed to perform processing based on such function to produce a diagnosis.

Although the sensor 54' is shown as incorporating one or more cantilever beams 80, the MEMs device may incorporate one or more diaphragms or other MEMs elements without departing from the scope of the invention as will be appreciated.

In another embodiment of the invention, the MEMs sensor 54' includes a surface which comprises a MEMs based acoustic pulse generator and receiver. The generator generates acoustic pulses that must travel through the fluid phase (e.g., blood) before being received by the receiver within the sensor 54'. The transmitter 60 obtains time-of-flight data for the pulses. Such time-of-flight data is indicative of how the composition settling on the surface of the sensor 54' changes (e.g., collagen, etc.).

As described above in relation to the SAW based sensor 54, the MEMs sensor 54' also may include a thin coating of the same or similar material used to make the input device so as not to create an atypical environment. Alternatively, a coating material for tailoring the response of the sensor 54' may be included consistent with the principles described above.

The present invention has been described primarily in the context of a graft 50 incorporating a sensor for detecting the accretion of biological material thereon. It will be appreciated, however, that other types of implants are equally applicable and the invention is not necessarily limited to a particular implant. For example, the aspects of the invention described above equally apply to a stent and are represented by the same drawings (with the exception that the vessel 52 would be contiguous in FIG. 2). Also, the implant device may be the sensor itself and need not be part of another device (such as a graft or stent) having its own independent function. The sensor in such case may be part of a capsule structure or the like which is retained within the body of the patient 34 for monitoring the buildup of biological matter.

Additionally, the above discussion has been concerned primarily with detecting the buildup of restenosis. It will be appreciated, however, that accretion of other types of biological matter may be detected in accordance with the present invention. For example, the sensor 54 may be configured with various hemosorbent or bound inhibitor coatings so as to be sensitive to toxin buildup in the blood stream; immune response factors in the blood stream; viral/DNA/bacterial entities; antibodies to some of the aforementioned; wear particles from joints, etc. Other types of accretion of biological matter that the sensor 54 may be configured to measure include lymphatic contaminants like bacteria, cancer cells, etc. Also, molecular species like enzymes and other dissolved components that may be present in urinary or lymphatic systems or airways (lungs, trachea, etc.) may be detected.

The function according to which the output of the sensor 54 or 54' varies compared to the build up of the particular matter of interest can be ascertained via empirical data, modeling, etc. The system 30 is programmed to apply such information in order to produce a diagnosis which indicates the relative health of the patient 34. Trending based on the output of the sensor 54 or 54' can be performed, and the health of the patient can be evaluated over time.

Referring back to FIG. 2, variations in the manner in which a SAW or MEMs based sensor 54/54' are utilized within an implant device are further contemplated as within the scope of the invention. For example, the MEMs sensor 54' may be a MEMs sensor designed to be responsive to acoustic sounds within the stent or graft 50. The sensor 54' includes one or more cantilevered beams 80 having a mechanical resonance in the acoustic band. The MEMs sensor 54' thus serves as a piezoelectric microphone which directly records sounds within the blood vessel, for example. Such sounds may be stored in memory in the transmitter 60 and subsequently transmitted outside the body of the patient. Alternatively, such sounds may be transmitted by the transmitter 60 substantially in real time to the receiver which in turn stores/analyzes the output of the sensor 54'. For example, by analyzing the frequency content of the detected sound for signs of turbulence, etc., increased occlusion can be detected.

In another embodiment of the invention, the implant device 32 may be an artificial joint such as a hip or knee. The SAW or MEMs based sensor 54/54' may be used to detect the build up of biological matter in the manner described above. Alternatively, the sensor 54/54' may be constructed so as to detect wear in friction coatings of the artificial joint. In such case, the sensor 54/54' is positioned at a location in the joint which incurs wear. The sensor 54/54' surface includes a coating generally consistent with the coating elsewhere in the joint. As the coating wears, the output of the sensor 54/54' will vary. This information can be analyzed externally via the same principles discussed above.

Alternatively, the sensor 54/54' may be configured to produce an output which varies as a function of the local temperature. By measuring the temperature remotely, one is able to determine a level of inflamation of tissue around the implant. Further still, the sensor 54/54' may include a strain or displacement sensing configuration. Such a sensor allows for measurement of structural loads (strain or displacement) on tissue/bone attached to the implant 30.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. An implant device, comprising:

a structure implantable within a living animal;

a sensor included as part of the structure, the sensor being operatively configured to detect accretion of biological material on the sensor by producing an output which varies as a function of the accretion of biological material on the sensor; and a communication element included as part of the structure and operatively coupled to the output of the sensor, the communication element being configured to communicate information based on the output of the sensor wirelessly to a remote element located outside the living animal.

2. The implant device of claim 1, wherein the sensor comprises at least one of a surface acoustic wave (SAW) device and a micro-electro-mechanical (MEMs) device.

3. The implant device of claim 1, wherein the communication element comprises at least one of an active transmitter and a passive sensing circuit.

4. The implant device of claim 1, wherein the structure comprises at least one of a stent and a graft and the sensor is located on an inner surface of the structure along which blood is intended to flow.

5. The implant device of claim 4, wherein the sensor includes an overlying film which exhibits a susceptability to buildup of restenosis at a rate approximately equivalent to other areas of the structure along which blood is intended to flow.

6. The implant device of claim 5, wherein the sensor comprises a SAW device.

7. The implant device of claim 5, wherein the sensor comprises a MEMs device.

8. The implant device of claim 1, wherein the sensor comprises a MEMs device which includes at least one cantilever beam, and the output of the sensor is a function of an amount of biological matter which adheres to the at least one cantilever beam.

9. A diagnostic system, comprising:

a structure implantable within a living animal;

a sensor included as part of the structure, the sensor being operatively configured to detect accretion of biological material on the sensor by producing an output which varies as a function of the accretion of biological material on the sensor;

a communication element included as part of the structure and operatively coupled to the output of the sensor, the communication element being configured to communicate information based on the output of the sensor wirelessly to a remote element located outside the living animal;

the remote element configured to receive the information from the communication element outside the living animal; and a processor for processing the information received by the remote element based on the function to provide a diagnostic output.

10. The system of claim 9, wherein the sensor comprises at least one of a surface acoustic wave (SAW) device and a micro-electro-mechanical (MEMs) device.

11. The system of claim 9, wherein the communication element comprises at least one of an active transmitter and a passive sensing circuit, and the remote element comprises at least one of a receiver and an excitation element.

12. The system of claim 9, wherein the structure comprises at least one of a stent and a graft and the sensor is located on an inner surface of the structure along which blood is intended to flow.

13. The system of claim 12, wherein the sensor includes an overlying film which exhibits a susceptability to buildup of restenosis at a rate approximately equivalent to other areas of the structure along which blood is intended to flow.

14. The system of claim 13, wherein the sensor comprises a SAW device.

15. The system of claim 13, wherein the sensor comprises a MEMs device.

16. The system of claim 9, wherein the sensor comprises a MEMs device which includes at least one cantilever beam, and the output of the sensor is a function of an amount of biological matter which adheres to the at least one cantilever beam.

17. The system of claim 9, wherein the sensor comprises a MEMs device including an acoustic pulse generator and receiver.

* * * * *